US 7,843,568 B2

(12) United States Patent
Kivela (10) Patent No.: US 7,843,568 B2
(45) Date of Patent: Nov. 30, 2010

(54) ENHANCED INSTRUMENTATION AND METHOD FOR OPTICAL MEASUREMENT OF SAMPLES

(75) Inventor: Petri Kivela, Piispanristi (FI)

(73) Assignee: Wallac Oy, Turku (FI)

( * ) Notice: Subject to any disclaimer, the term of this patent is extended or adjusted under 35 U.S.C. 154(b) by 0 days.

(21) Appl. No.: 12/692,758

(22) Filed: Jan. 25, 2010

(65) Prior Publication Data

US 2010/0123088 A1    May 20, 2010

Related U.S. Application Data

(62) Division of application No. 11/662,468, filed as application No. PCT/FI2004/000525 on Sep. 10, 2004, now abandoned.

(51) Int. Cl.
*G01N 21/25* (2006.01)

(52) U.S. Cl. .................. 356/417; 356/317; 356/318; 356/73

(58) Field of Classification Search ................. 356/417, 356/317, 318, 73; 250/458.1
See application file for complete search history.

(56) References Cited

U.S. PATENT DOCUMENTS

| 4,778,763 | A | 10/1988 | Makiguchi et al. |
| 5,780,857 | A | 7/1998 | Harju et al. |
| 6,538,735 | B1 | 3/2003 | Duebendorfe et al. |
| 6,555,802 | B2 * | 4/2003 | Osipchuk et al. ......... 250/201.3 |
| 6,563,584 | B1 | 5/2003 | Yurino et al. |
| 7,199,879 | B2 | 4/2007 | Harju et al. |

| 2002/0043626 | A1 | 4/2002 | Booker et al. |
| 2004/0057870 | A1 * | 3/2004 | Isaksson et al. ............... 422/52 |

FOREIGN PATENT DOCUMENTS

| EP | 1400801 | 3/2004 |
| JP | 11 094747 A | 4/1999 |
| JP | 2000-321206 | 11/2000 |
| WO | 95/11441 A1 | 4/1995 |

OTHER PUBLICATIONS

"AlphascreenTM" Announcement Perkin Elmer Cetus, Jan. 1, 2003, pp. 1-12, XP002272309.
European Search Report in Corresponding Application EP 09179076 Dated Jan. 21, 2010.

(Continued)

*Primary Examiner*—L. G Lauchman
(74) *Attorney, Agent, or Firm*—Young & Thompson (57) ABSTRACT

The present invention relates generally to the field of biochemical laboratory instrumentation for different applications of measuring properties of samples on e.g. microtitration plates and corresponding sample supports. The object of the invention is achieved by providing an optical measurement instrumentation wherein a sample (281-285) is activated (212AS, 218AS) and the emission is detected (291, 292), wherein between the activation and detection phases of measuring the sample, a shift is made in the relative position between the sample and means (218) directing the activation radiation to the sample as well as in the relative position between the sample and the means (293) receiving the emission radiation from the sample. This can be implemented e.g. by moving (299) the sample assay plate and/or a measuring head between the activation and emission phases of a sample. The invention allows a simultaneous activation of a first sample and detecting emission from a second sample thus enhancing efficiency of the measurement.

26 Claims, 6 Drawing Sheets

OTHER PUBLICATIONS

Warner Greg et al:, "Alphascreen Kinase HTS Platforms.", Current Medicinal Chemistry. Mar. 2004, vol. 11, No. 6, Mar. 2004, pp. 721-730, XP0099047358, ISSN:, 0929-8673, The Whole Document.

Seethala R:, "C Alpha Screen", Handbook of Drug Screening, 2001, pp. 106-128, XP008028242, p. 106-p. 110; Figures 18-20.

Nakazawa, T., "Analysis of protein interaction using multi label plate reader", Protein, Nucleic Acid and Enzyme, 2004, pp. 1777-1780, vol. 49, No. 11, Perkin-Elmer Corp., Japan.

JP Office Action dated May 19, 2010 in corresponding JP 2007-530724.

* cited by examiner

ENHANCED INSTRUMENTATION AND METHOD FOR OPTICAL MEASUREMENT OF SAMPLES

CROSS REFERENCE TO RELATED APPLICATIONS

This application is a division of co-pending application Ser. No. 11/662,468 filed on May 14, 2007, which is the 35 U.S.C. §371 national stage of International PCT/FI04/00525 filed on Sep. 10, 2004. The entire contents of each of the above-identified applications are hereby incorporated by reference. Any disclaimer that may have occurred during prosecution of the above referenced applications is hereby expressly disclaimed.

BACKGROUND OF THE INVENTION

The present invention relates generally to the field of biochemical laboratory instrumentation for different applications of measuring properties of samples on e.g. microtitration plates and corresponding sample supports. More particularly the invention relates to more efficient, instrumental features of equipment used as e.g. fluorometers, photometers and luminometers. The applications may be e.g. clinical or research applications.

The routine work and also the research work in analytical biochemical laboratories and in clinical laboratories is often based on different tags or labels coupled on macromolecules under inspection. The typical labels used are different radioactive isotopes, enzymes, different fluorescent molecules and e.g. fluorescent chelates of rare earth metals.

The detection of enzyme labels can be performed by utilizing its natural biochemical function, i.e. to alter the physical properties of molecules. In enzyme immunoassays colourless substances are catalysed by enzyme into colourful substances or non-fluorescent substances to fluorescent substances.

The colourful substances are measured with absorption, i.e. photometric measurement. In the photometric measurement the intensity of filtered and stabilized beam is first measured without any sample and then the sample inside one plate is measured. The absorbance i.e. the absorption values are then calculated.

The fluorescent measurement is generally used for measuring quantities of fluorescent label substance in a sample. The most photoluminescence labels are based on molecular photoluminescence process. In this process optical radiation is absorbed by the ground state of a molecule. Due to the absorption of energy the quantum molecule rises into higher excited state. After the fast vibrational relaxation the molecule returns back to its ground state and the excess energy is released as an optical quantum. Due to losses in this process the average absorbed energies are higher than the average emitted energies. In the following, "activation" is used as a term including excitation of photoluminescence as well as other types of activation by radiation as is described below.

A further measurement method is chemiluminescence measurement where emission of a substance is measured from a sample without activation by illumination. Thus a photoluminometer can also be used as a chemiluminometer.

Further, there is an analysing method called Amplified Luminescent Proximity Homogeneous Assay or AlphaScreen™. The function of the AlphaScreen™ method is based on the use of small beads that attach to the molecules under study. There are two types of beads that are coated with a material acting either as a donor or acceptor of singlet-state oxygen. The measurement starts, when the liquid sample is illuminated by light with wavelength of 680 nm. After this the material in the donor bead converts ambient oxygen into singlet-state oxygen. The single-state molecules have a short lifetime and they can reach only about a 200 nm distance by diffusion in the liquid. If the chemical reaction in question has taken place, both the donor and acceptor beads are bound to the same molecule and so they are close to each other. In this case the singlet-state oxygen may reach the acceptor bead where a series of reactions is started. As the last phase of the reaction the coating material in the acceptor beads emits photons in the 500-700 nm range. If the chemical reaction has not taken place the singlet-state oxygen cannot reach the acceptor bead and the emission light is not detected. By measuring the intensity of light it is possible to conclude the efficiency of the chemical reaction.

The typical instruments in analytical chemical research laboratories are the different spectroscopic instruments. Many of them are utilizing optical region of electromagnetic spectrum. The two common types of instruments are the spectrophotometers and the spectrofluorometers. These instruments comprise usually one or two wavelength dispersion devices, like monochromators. The dispersion devices make them capable to perform photometric, photoluminescence and chemiluminescense measurements throughout the optical spectrum.

Figure 1:
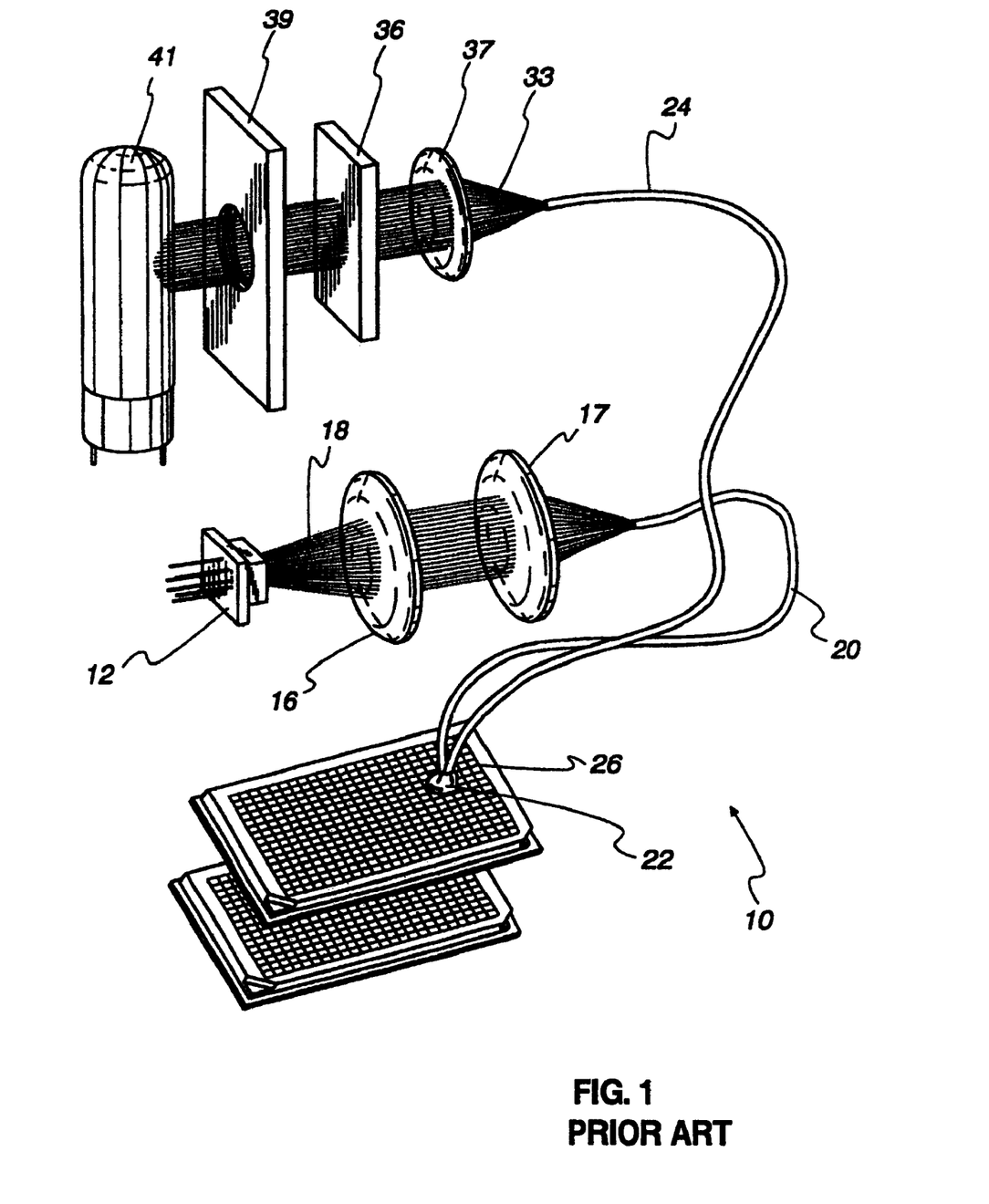
FIG. 1 is a schematic block diagram of a prior art optical unit of a measurement instrument.

Patent document U.S. Pat. No. 6,538,735 describes a prior art device for detecting emission from samples. The principle of the device is illustrated in FIG. 1. In the device 10 the sample is illuminated by high intensity light produced by a light source 12 such as a laser diode. The light transmitted via a fibre bundle 20 activates the sample, which converts the activation light into emission light upon biomolecular binding occurrence. The emitted light is transmitted via a fibre bundle 24 to a detector 41, such as a photomultiplier tube, which detects and measures the amount of light after activation ceases. The fibre bundles that transmit light at the activation and emission wavelength bands are combined such that the common end of the bundle directly above the well includes both fibre types. The fibres may be combined e.g. coaxially. The system can also include a band-pass filter 36 on the emission side, which eliminates extraneous light, including light corresponding to the activation wavelength band. The system can be used in assays based on Amplified Luminescent Proximity Homogeneous Assay technique. The amount of light produced by the sample is proportional to the concentration of an analyte in the sample.

The activation wavelength is between 670 to 690 nm. The light can be generated by employing a high-intensity laser as the activation source, emitting in the preferred wavelength region. The light emitted from the sample has a wavelength band between about 520 nm and 620 nm. This range is at a shorter wavelength than that of the activation wavelength band. The device may include a shutter that prevents light from entering the detector while the laser diode is active, and a filter may prevent light outside the emitted wavelength band from entering the detector.

The emitted signal of the AlphaScreen™ measurement is weak, and the measurement is sensitive to changes in the environment. Therefore it is difficult to achieve an efficient and accurate apparatus for the AlphaScreen™ measurement. Therefore there are certain problems related to the prior art arrangements, especially if several types of measurements are performed with same equipment.

The described prior art arrangement of FIG. 1 uses a coaxial optical cable for transmission and detection. When the cross-section of the cable is used for separate optical wires for activation and detection the usable cross section area is very limited. Therefore both the activation light pulse and the emission light are much attenuated. The attenuation of the activation and emission radiation naturally degrades the efficiency and accuracy of the measurements. The attenuation also causes that the instrument needs more calibration.

One solution could be using a dichroic mirror for separating the optical paths of activation and detection beams as is often used photoluminescence measurements. A prior art arrangement for providing photoluminescence measurements is described e.g. in patent document U.S. Pat. No. 6,071,748. However, there would be further problems if photoluminescence measurement equipment would be used also for AlphaScreen™ measurement. Firstly, if a part of the confocal optics is same for illumination and detection, it can be optimised for only one of these purposes. When a sensitive measurement like AlphaScreen™ is performed it would be important that the optics would be optimised for both illumination and detection. Secondly, different type illumination sources are used in AlphaScreen™ and photoluminescence measurements, and therefore it would be necessary to have optical switches for switching the optical route between two light sources. However, optical switches and the related optics attenuate radiation and therefore decrease the efficiency of the measurements. Good quality optical switches also tend to increase the manufacturing costs of the instrument.

A further significant problem relates to the efficiency of the prior art solutions. In the AlphaScreen™ measurement it is advantageous to use relatively long emission and detection times for each sample. Therefore it takes a long period of time to provide measurements for a whole sample well plate that has a large number of samples. And if several types of measurements are made for the same samples length of the measurement time increases further. The long measurement time naturally means that the throughput of the measurement equipment is not very high. And it also brings a problem that it may be difficult to keep the environmental conditions, such as temperature, sufficiently stable during the measurement of a whole sample assay.

Patent documents U.S. Pat. No. 6,563,584 and U.S. Pat. No. 4,778,763 describe solutions in which a sample is activated with activation light from an excitation light source and then the sample is transported to an optical axis of a detector that measures radiation emitted by the sample. These arrangements are, however, not suitable for such measurements in which an activation of a sample and a detection of radiation emitted by the sample have to be performed simultaneously.

SUMMARY

An object of the present invention is to provide an optical instrument for laboratory measurements, wherein the described disadvantages of the prior art are avoided or reduced. The object of the invention is therefore to achieve a measurement instrument with improved versatility, accuracy, reliability and/or efficiency for performing measurements from samples.

The object of the invention is achieved by providing an optical measurement instrumentation wherein a sample is activated and the emission is detected from the activated sample, and between the activation and detection phases in measuring the sample, a shift is made in the relative position between the sample and means directing the activation radiation to the sample as well as in the relative position between the sample and the means receiving the emission radiation from the sample. This can be implemented e.g. by moving the sample assay plate and/or a measuring head between the activation and emission phases. The invention allows a simultaneous activation of a first sample and detecting emission from a second sample.

The present invention has several advantages over prior art solutions. Since the activation beam and the emission beam have separate optical paths it is possible to optimise the optics for illumination and detection separately. Thus the accuracy and the efficiency of the measurement are enhanced. The efficiency of the measurement is also increased by the fact that the activation and the detection can be performed simultaneously. It is also possible to perform different types of measurements simultaneously, such as photoluminescence measurements and AlphaScreen™ measurements. This enhances the overall efficiency further. The accuracy of the measurement is also enhanced by the fact that a whole sample plate can be measured in minimal time, and the environmental conditions can thus be kept stable. As a further advantage, very few optical components are needed for performing sensitive AlphaScreen™ measurements and thus optical attenuation is small and manufacturing is cost of the instrument is moderate.

In accordance with the first aspect of the invention there is provided a new optical measurement instrument for measuring samples. The optical measurement instrument according to the first aspect of the invention comprises:
an illumination source for producing activation radiation,
a detector for measuring emission radiation, and
shifting means for changing relative position of the samples with respect to the illumination source and the detector, wherein the shifting means are disposed to change the relative position of the samples with respect to the illumination source and the detector in a stepwise manner from a first relative position, in which the detector is capable of measuring the emission radiation from a first sample and the illumination source is capable of producing the activation radiation into a second sample, to a second relative position, in which the detector is capable of measuring the emission radiation from the second sample and the illumination source is capable of producing the activation radiation into a third sample.

In accordance with the second aspect of the invention there is provided a new method for measuring samples. The method according to the second aspect of the invention comprises:
producing activation radiation with an illumination source,
measuring emission radiation with a detector, and
changing relative position of the samples with respect to the illumination source and the detector in a stepwise manner from a first relative position, in which the detector is capable of measuring the emission radiation from a first sample and the illumination source is capable of producing the activation radiation into a second sample, to a second relative position, in which the detector is capable of measuring the emission radiation from the second sample and the illumination source is capable of producing the activation radiation into a third sample.

Some preferred embodiments are described in the dependent claims.

BRIEF DESCRIPTION OF THE DRAWINGS

The described and other advantages of the invention will become apparent from the following detailed description and by referring to the drawings where.

FIG. 1 was already explained in the description of the prior art. In the following, the principle of the invention is first described referring to FIG. 2. Then, an example of a more detailed implementation is described referring to FIGS. 3 and 4, which illustrate main parts of an exemplary analyser equipment according to the invention. Finally, an exemplary method according to the invention is described referring to FIGS. 5 and 6.

DETAILED DESCRIPTION OF THE EMBODIMENTS

Figure 2:
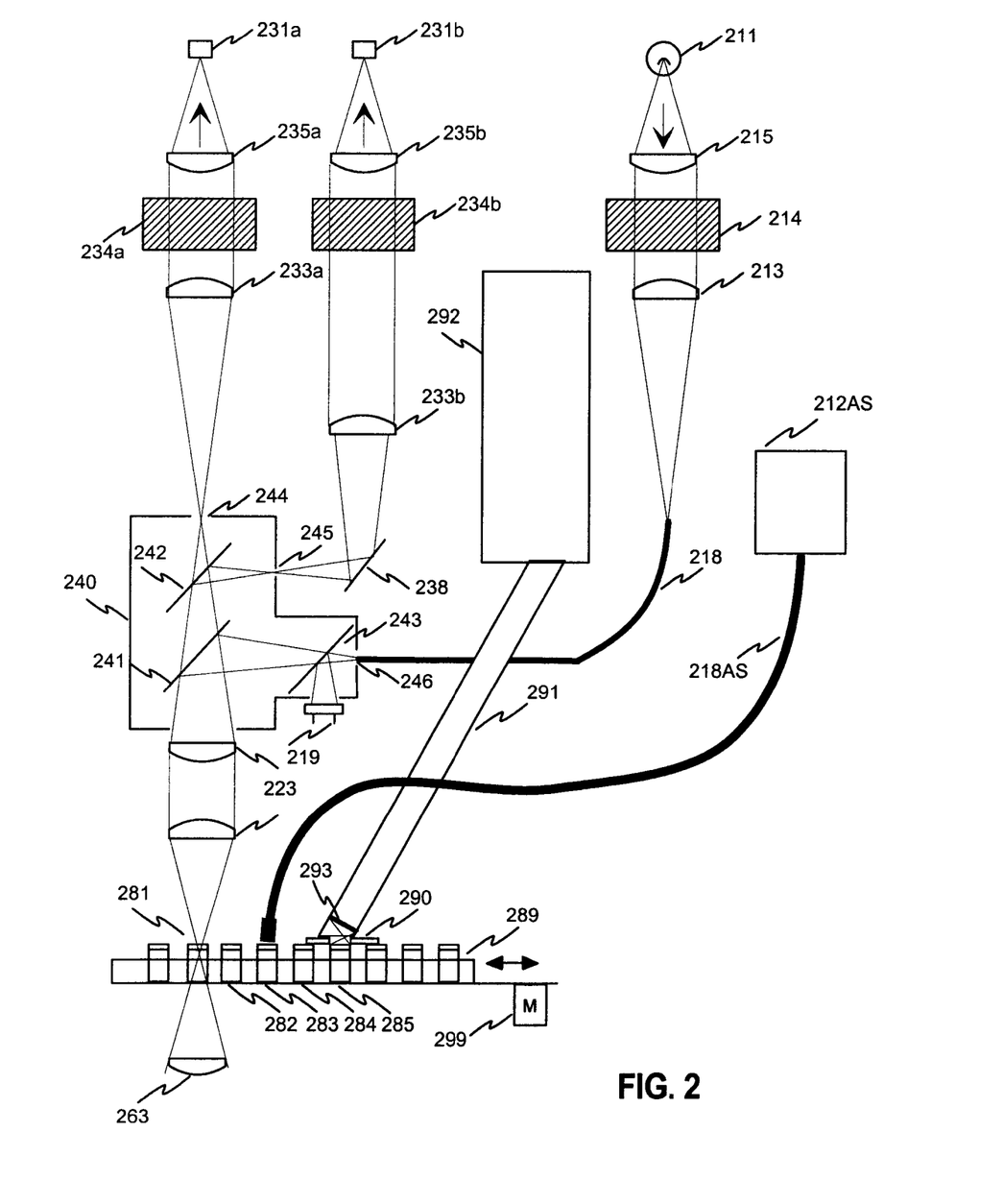
FIG. 2 is a schematic illustration of optical paths and main components of an exemplary optical unit for a measurement instrument according to the invention.

FIG. 2 illustrates main components and optical paths of an exemplary optical analyser instrument according to the invention. This versatile instrument comprises means for performing both ordinary type photoluminescence measurements as well as measurements according to the invention for e.g. AlphaScreen™ measurements. Next the parts for ordinary photoluminescence measurement are first described, and then the parts for e.g. the Alphascreen™ measurement.

The instrument comprises an illumination source 211 for the activation of a sample in a photoluminescence measurement. The radiation from the lamp 211 is collimated with lens 215 and directed through an interference filter 214. Different filters can be selected for different wavelengths. The activation beam is then focused with a lens 213 to an end of a fibre optic guide 218, which guides it to an aperture 246 of an optical module. The fibre optic guide is preferably a bundle of fibres, such as 200 pieces of fibres with a diameter of 100 µm.

The activation beam is guided through an aperture 246 of the optical module and reflected by a dichroic mirror 241 inside the optical module 240. The activation beam is further directed into the sample 281 through an aperture of the optical module and a lens system 223. A part of the illumination light is reflected by a beam splitter mirror 243 and guided through an aperture into a reference detector 219 in order to give reference information on the actual illumination intensity. A beam splitter mirror can be produced e.g. by forming reflective coating for the mirror to be e.g. stripes or dots, which cover only a part of the mirror surface.

The photoluminescence emission beam from the sample 281 is directed with the lens system 223 through an aperture into the optical module 240, where it passes the dichroic mirror 241. The dichroic mirror is can be designed for a certain label so that it reflects activation wavelength but transmits emission wavelengths. The emission beam is then divided inside the optical cube into to two beams by a second mirror 242. The mirror is preferably a dichroic mirror, which functions as a filter so that a beam with a wavelength of the first emission is transmitted through the mirror and focused through an aperture 244 to the first detector 231a. The beam with a wavelength of the second emission is reflected and guided focused through another aperture 245 to the second detector 231b. The second dichroic mirror is therefore designed for each label/pair of labels so that it transmits first emission wavelengths but reflects second emission wavelengths.

The first emission beam received from the aperture of the optical module is collimated with a lens 233a and directed through an interference filter 234a in order to prevent light with a wavelength outside the first emission from passing to the first detector. The first emission beam is then focused with lens 235a to the first detector 231a. The second emission beam received from another aperture of the optical module is reflected with a mirror 238 to a lens 233b where the beam is collimated and directed through a second interference filter 234b in order to prevent light with a wavelength outside the second emission from passing to the second detector. The second emission beam is then focused with lens 235a to the first detector 231a. The signals received from the detectors are then amplified and processed to achieve a value for the intensities of the first and second emissions. The instrument may also comprise a bottom measurement head for measuring radiation below the sample, via lens 263.

When the instrument of FIG. 2 is used for e.g. AlphaScreen™ measurement the activation light is received from the laser source 212AS, and the beam is directed via an optical guide 218AS to a sample 283. The fibre optic guide is preferably a bundle of fibres, such as 1000 pieces of fibres with a diameter of 100 µm. One purpose of the fibre optic guide is to mix the light of the illumination source in order to avoid an uneven distribution of activation beam within the sample volume to be measured. The fibre optic guide is preferably of such a width that it exactly illuminates the whole sample. If the fibre optic guide has a smaller or wider diameter than the sample, a lens system can be used at the end of the fibre optic guide to adjust the diameter of the activation light beam to illuminate the whole sample.

The instrument comprises a detector 291 for AlphaScreen™ measurements. In this embodiment the detector is a photo-multiplier tube. The photo-multiplier may preferably be also used for chemiluminescence measurements. The photo-multiplier tube is in this example in a slightly tilted orientation. This may be necessary in order to perform simultaneously different types of measurements from samples that are near to each other on a sample plate.

The detector receives the radiation from the sample 283 via an aperture of a disk 290. The radiation reaches the window 293 of the photo-multiplier tube, and after penetrating through the window the radiation reaches the active surface of the photo-multiplier tube. The block 292 includes the preamplifier and other related electronics for the photo-multiplier tube for measuring the intensity of the received radiation.

It is advantageous in the AlphaScreen™ measurement that the detector is near to the sample, and the radiation has a clear, direct path from the sample to the detector. Thus the attenuation of the emission radiation is negligible. It is also possible to achieve low attenuation for measuring chemiluminescence emission beam the described instrumentation. The advantages of the invention become more apparent in the following more complete example of an optical instrument according to the invention.

The present invention is implemented by e.g. first activating a certain sample (281-285) and then shifting the position of the sample plate in relation to the illumination directing means 218AS and photo-multiplier tube 291, 293 in order to measure the emission. There is a processor-controlled motor 299 for performing the shifting of the sample plate 289 between illumination and detection phases of each sample.

It would also be possible to include more than one illumination source and detector for the measurement according to the invention. Using several illumination source—detector pairs would naturally increase the measurement efficiency further as simultaneous activation and detection of several samples would be possible. It would also be possible to have two or more adjacent detectors for detecting sequentially emission of same samples. Thus a sample would be first activated, and after shifting the sample plate/measurement head the emission would be first detected with a first detector, and after further shifting the sample plate/measurement head the emission of the same sample would be detected with a second detector etc. This way a more accurate measurement result would be achieved.

Figure 3:
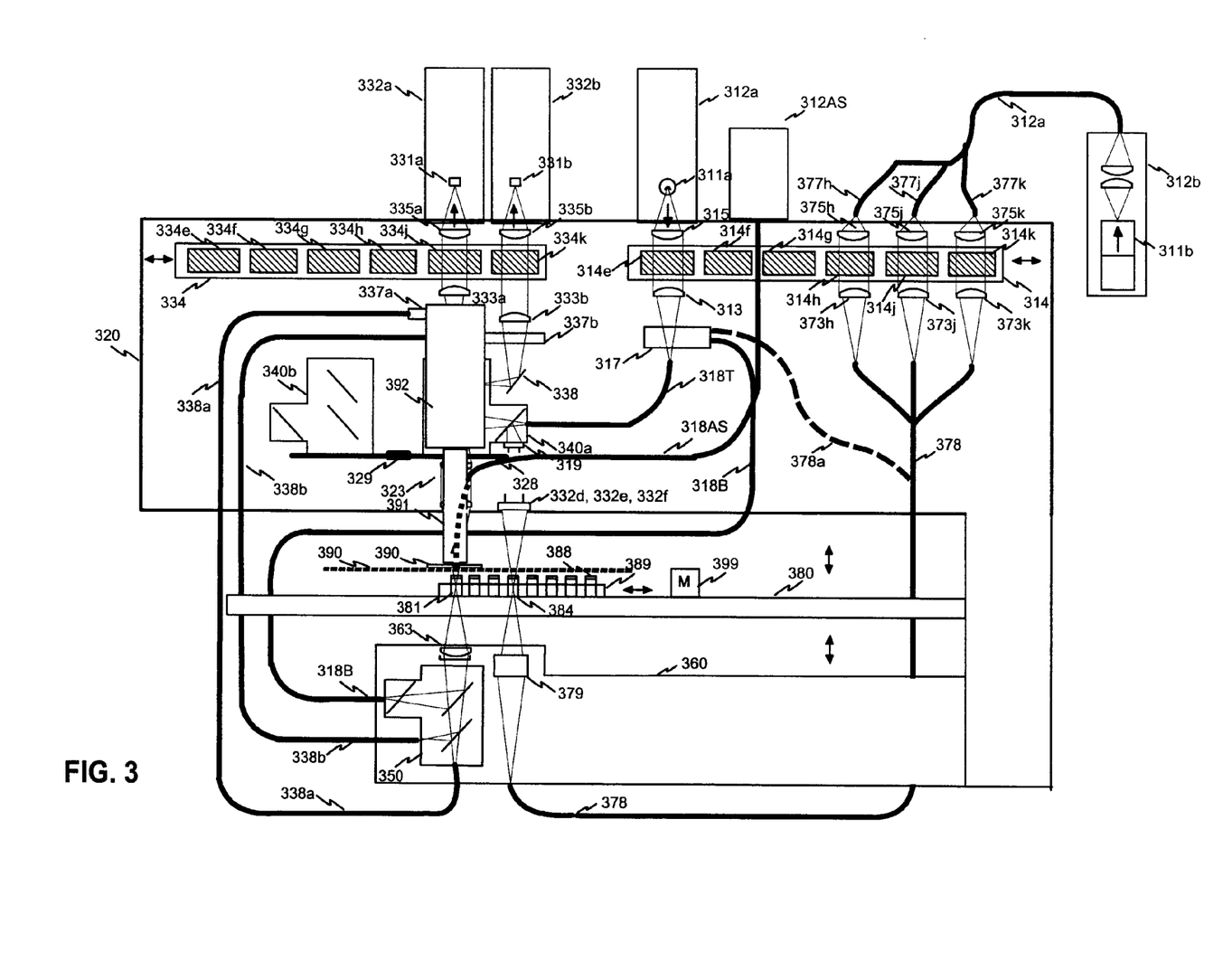
FIG. 3 is a schematic block diagram including a side view of an exemplary measurement instrument according to the invention where several measurement modes are available.

FIG. 3 illustrates in more detail an exemplary optical instrument according to the invention. Especially, an implementation of an instrument for several alternative measurement modes is illustrated in more detail. This shows how the present invention allows an effective combination of measurement modes in a single equipment.

The instrument of FIG. 3 has a top measurement head 320, which includes components for providing an activation beam and for detecting emissions from above the sample. The instrument has also an optional bottom measurement head 360, which includes components for providing an activation beam and for detecting emissions from below the sample. The means according to the present invention for directing activation and/or detection to samples can be included in the top and/or bottom measurement head. The instrument further comprises a sample platform 380, which has means for moving a sample tray 389 in order to position successive samples 381 into the measurement locations. There may also be means provided for adjusting the vertical position of the sample platform relative to the top and bottom measurement heads.

The instrument comprises a laser source 312AS for e.g. AlphaScreen™ measurements The laser source is advantageous due to its high efficiency on a narrow range of wavelengths. However, also other illumination sources are applicable, such as Xenon or halogen lamp used with a filter. The light of the laser source 312AS is guided in an optical guide 318AS directly to the sample. According to the present invention the relative position between the sample tray and the measurement head is changed between the illumination and detection phases of samples.

The instrument comprises a detector 391 for detecting the emission signal in AlphaScreen™ measurements. The detector may also be used for chemiluminescence measurements. In this embodiment the detector is a photo-multiplier tube. The detector receives the radiation from the sample via an aperture of a disk 390. The AlphaScreen™ detector is in front of the photoluminescence components, and thus the AlphaScreen™ measurement is made from a sample which is more on the front, whereas the photoluminescence measurement is made from a sample which is more on the back in FIG. 3. The fibre optic guide providing the laser activation is located between the photomultiplier tube 391 and the optics for the photoluminescence measurement. Thus a photoluminescence measurement and an AlphaScreen™/chemiluminescence measurement can be performed simultaneously from different samples.

The detector 391 can be used in analogue mode or digital mode, or if the properties of the photo-multiplier tube allow, both modes may be used simultaneously. The preamplifier and other related electronics for the photo-multiplier tube are located in a housing 392 above the photo-multiplier tube.

The aperture discs may be changeable so that different size apertures can be used with different sample plates. They may preferably be equipped with machine readable codes, such as bar codes, so that the processor of the equipment can check with a code reader, which type of aperture disk is installed. This way it can be certified that a correct type of aperture disk is used for each measurement. The bar code reader or related electronics are not shown in FIG. 3.

The instrument may also comprise a thermo plate 390 for keeping the temperature of the samples constant during the AlphaScreen™ measurements. The upper measurement head 320 or the sample platform 380 may be vertically shifted in order to have the thermo plate tightly between the assay and the upper measurement head.

Next the components for performing other types of measurements are shortly described. The instrument according to FIG. 3 has another illumination source 312a for providing activation in photoluminescence measurements. The illumination source 312a includes a pulse lamp, and the optical energy of each pulse is preferably equal. The activation beam generated by the pulse lamp is collimated with a lens 315 and directed through an interference filter 314. The filter is placed on a filter slide, so that the activation filter to be used in a measurement can be selected from several filters. The activation beam is then focused to an end of a fibre optic guide 318, which mixes the activation beam and guides it to an aperture of an optical module 340a, which is located behind the photomultiplier tube. The optical module 340 and the lens system 323 directs the activation beam into the sample 381.

The equipment may also include a further pulse lamp 312b, 311b, which may be a low power lamp, e.g. for simultaneous photometric measurements. The instrument has an optical fibre guide 312a for guiding the light from the second lamp. The light can be distributed for the photometric measurement into three filters 314h, 314j and 314k with fibre branches 377h, 377j and 377k. After filtering, the beams are collimated into ends of three optical fibre cables 378, which are led to the bottom measurement head for the photometric measurement. The light beams from the optical cables 378 are focused to three samples 384 with a lens system 379 including lenses for each three beams. After transmitting through the samples the beams are measured with three detectors 322d, 322e and 322f, which are e.g. a photo diodes. The three ends of the fibre optic cables, three lenses, three simultaneously measured samples and three detectors are in this case located in a row perpendicular to the plane of the drawing and thus only one of them can be seen in the drawing.

It is also possible to use an instrument with same pulse lamp for photometrics and photoluminescence measurements. For example, an optical switch 317 may have an output for an optical fibre 378a, which leads light from the lamp 312a to the photometrics measurement optics 379. It is then possible to control the optical switch either to guide the light for providing activation for an emission measurement or to guide the light the a photometric measurement.

An optical fibre 318T is used for guiding the activation beam from the optical switch 317 to the optical module 340 of the top measurement head. An optical fibre 318B is used for guiding the activation beam from the optical switch 317 to the optical module 350 of the bottom measurement head. The instrument may also have a further lamp so that different lamps can be selected for providing the activation beam of the top head and the bottom head. In this case, a more versatile optical switch system is required.

The emission beam from the sample 381 is directed with the lens system 323 into the optical module 340 where the emission beam is divided into to two beams. A dichroic mirror in the optical module preferably functions as a filter so that a beam with a wavelength of the first emission is transmitted through the to the first detector 331a, and a beam with a wavelength of the second emission is reflected to the second detector 331b. When the equipment includes two detectors they may be of different types and there may be alternative detection modes for a photoluminescence measurement.

The first emission beam is collimated with a lens 333a and directed through an interference filter 334j in order to prevent light with a wavelength outside the first emission from passing to the first detector. The first emission beam is then focused with lens 335a to the first detector 331a. The second emission beam is reflected with a mirror 338 to a lens 333b where the beam is collimated and directed through a second interference filter 334k in order to prevent light with a wavelength outside the second emission from passing to the second detector. The second emission beam is then focused with lens 335a to the first detector 331a. The filters 334j and 334k are located on same filter slide or they may locate on different filter slides. The filter slide(s) is movable so that the filters used in the measurement can be selected from a number of filters with different pass-band wavelengths.

In an instrument also comprising a bottom measurement head there are optical switches 337a and 337b for selecting the detected emission beam from the top or bottom measurement head. An optical fibre 338a is used for guiding the first emission beam from the optical module 350 of the bottom measurement head 360 to the optical switch 337a. Another optical fibre 338b is used for guiding the second emission beam from the optical module 350 of the bottom measurement head 360 to the optical switch 337b.

The signals received from the detectors are amplified and processed to achieve a measurement value for the intensities of the emissions. Measurement signals and reference signals are amplified and read after each activation pulse and signal corrections are calculated. Basic references are determined with standard solvents after the analyzer has been assembled. Several emission signals from a same sample may be digitally integrated. Thus the instrument is also equipped with electronics for amplifying and processing the signals from the detectors, as well as electronics for driving the lamp(s). There is also control electronics provided for controlling the measurements, such as selecting filter(s), selecting the optical module(s), controlling optical switch(es), controlling the position of the sample tray 389 according to the invention for selecting the sample to be measured, and controlling the positions of the measurement heads 320 and 360 relative to the sample platform 380. The main electronics is not shown in FIG. 3, as the required electronics can be designed by a skilled person in the art using the teachings of the present invention.

Figure 4:
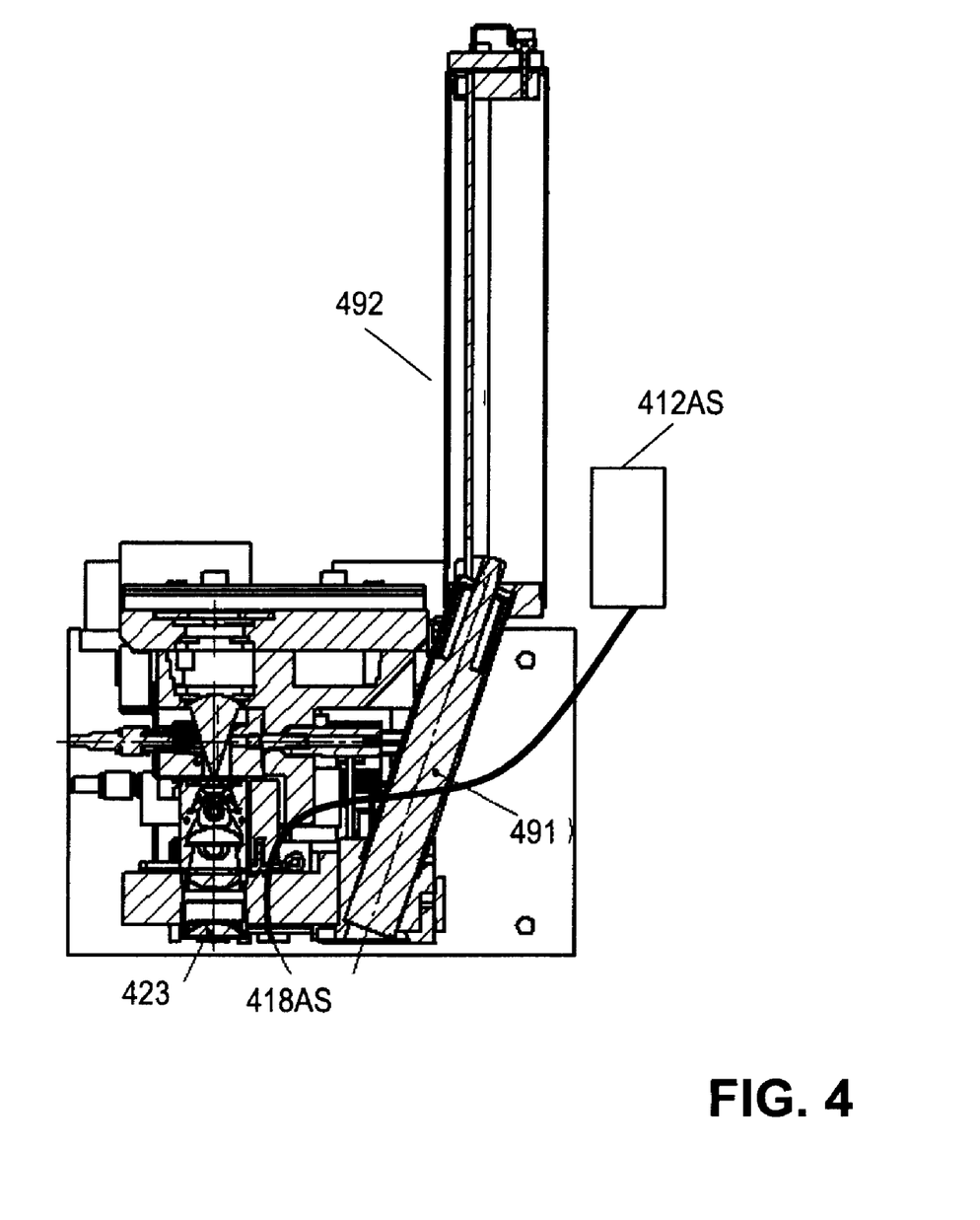
FIG. 4 is a front view of an exemplary top measurement head according to the invention.

The photo-multiplier tube and its electronics as well as the light sources are shown reduced in size compared to other components in FIG. 3. On the other hand, the optical modules are shown essentially enlarged in FIG. 3 in order to better illustrate the optical paths in the instruments. FIG. 4 illustrates the sizes in a more correct relation.

FIG. 4 illustrates a front view of an exemplary top measurement head according to the invention. The measurement head comprises optics 423 for photoluminescence measurements. It also comprises a photo-multiplier tube 491 with associated amplifier 492 for receiving and detecting emissions in AlphaScreen™ and chemiluminoscence measurements. Between the photoluminescence optics 423 and photo-multiplier tube 491 there is located a fibre optic guide 418AS for guiding activation light from a laser source 412AS to a sample in e.g. AlphaScreen™ measurements.

Figure 5:
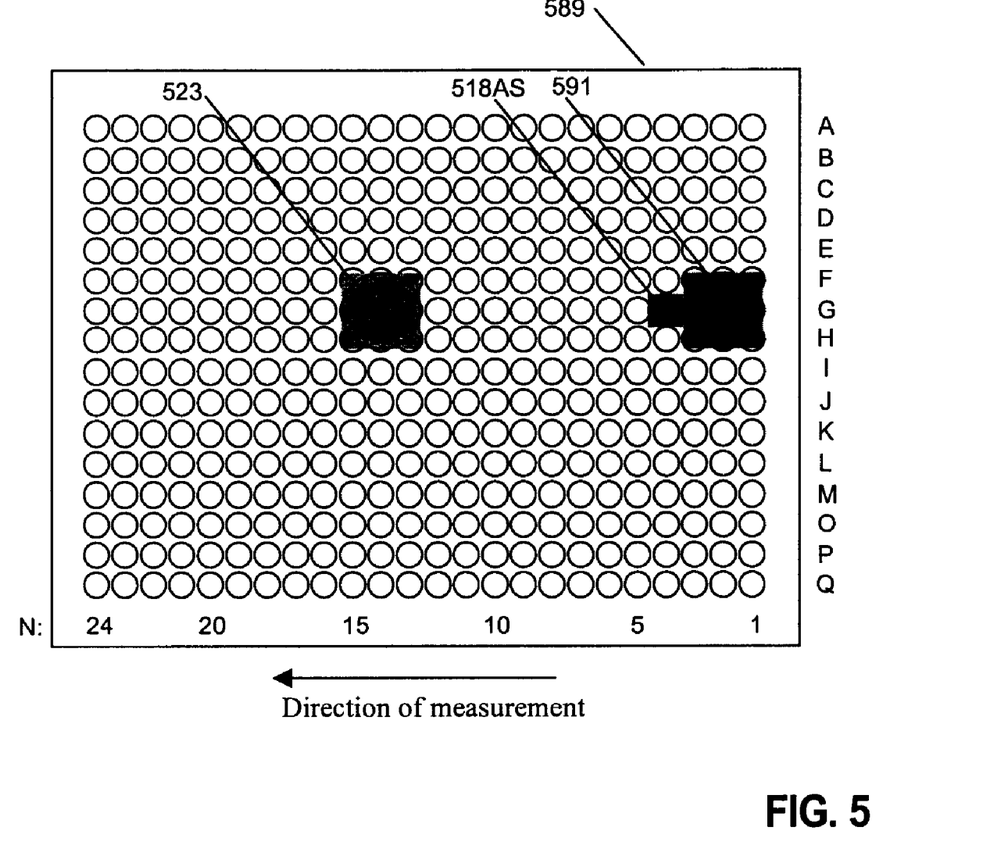
FIG. 5 illustrates a top view of a sample assay plate and shows above the samples an exemplary positioning of the optical means for the measurement according to the invention.
Figure 6:
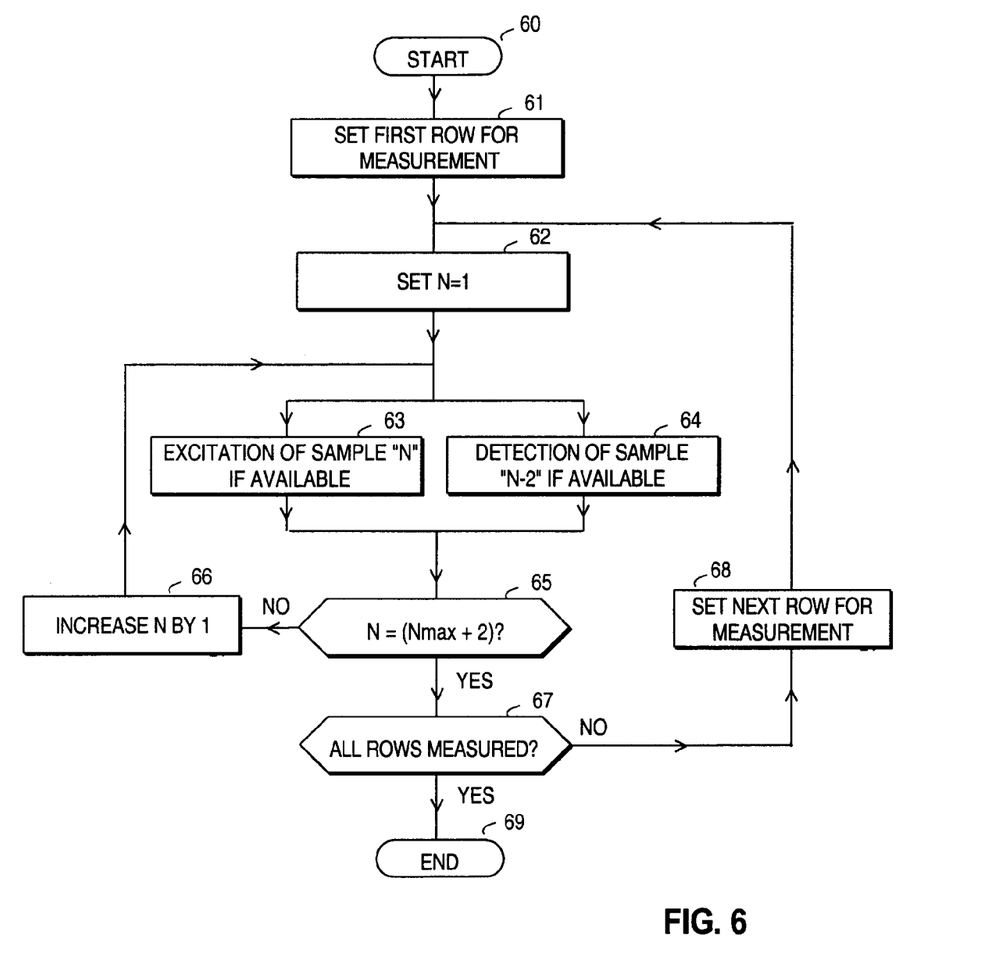
FIG. 6 is a flow diagram illustrating an exemplary method for performing an optical measurement according to the invention.

Next an example of a measurement method according to the invention is described referring to FIGS. 5 and 6. FIG. 5 illustrates a top view of a sample assay plate 589. It has sample wells in a 16×24 matrix with 16 rows A-Q and 24 lines (N). Fibre optic guide 518AS providing activation light for AlphaScreen™ measurements is above sample well G-4 in the Figure. The detector 591 for detecting Alphascreen™ and chemiluminescence emission is above sample well G-2. Due to the dimensions of the detector there is one sample well G-3 between the activation fibre and the detector. However, if dimensions allow, the activation fibre and detector may also be located above adjacent sample wells. FIG. 5 also shows the position of optics 523 for performing photoluminescence measurements.

If the AlphaScreen™ measurement starts at the position according to FIG. 5, the sample G-4 is first activated. Then the sample plate is shifted by one step in the right direction, or alternatively the measurement head is shifted by one step into the left direction. After this shifting the sample G-5 is activated. Next the sample plate or measurement head is again shifted by one step. After this, the sample G-6 is activated and emission from the sample G-4 is detected. The activation and detection are preferably simultaneous. This procedure of shifting, activation and detection is continuing until the last sample in the row (Nmax=24) is activated and detected. Then samples in other rows A-Q may be measured. Said "shift by one step" preferably means a shift of a distance between two adjacent samples. In some cases the shift may also be a multiple of said distance.

FIG. 6 illustrates a flow diagram of an exemplary method according to the invention for performing an AlphaScreen™ measurement of a sample assay plate.

When measurement of a sample assay plate starts, 60, the sample plate and measurement head are positioned for activating a sample in a first row and first sample N=1 in the row is to be activated, 61, 62. The sample N=1 is then activated, 63. There is no sample at the position of the detector (N−2), so detection 64 is not performed at this phase. In phase 65 it is checked whether all samples of the row are measured. If not, the sample plate or measurement head is shifted by one step ie. "N" is increased by one. Then sample 2 in the row is activated, 63, and N is again increased by one. When N has value 3 there is an activated sample at the position N−2=1 below the detector. Thus it is possible to perform simultaneously activation of sample N=3, 63, and detection of emission from sample N−2=1, 64. Thus the procedure continues by increasing the value of "N" in steps of one, 66, and performing simultaneous activation of sample N and detection of emission from sample N−2. When two last samples in the row are detected, there is no sample at the position of the laser optic guide, so activation is not performed in phase 63.

When all samples in a row are measured, it is checked whether all rows are measured, 67. If not, the measurement continues at the next sample row, 68. When all sample rows have been measured, 67, the measurement procedure is ended, 69.

In the above examples there is one sample well between the two samples to be simultaneously activated and detected. However, it would also be possible to have other number of sample wells between the two samples, starting from zero.

In this patent specification the structure of the components in an optical measurement instrument is not described in more detail as they can be implemented using the description above and the general knowledge of a person skilled in the art.

As mentioned above, an optical instrument includes control means for performing the optical measurement process. The control of the measuring process in an optical measurement instrument generally takes place in an arrangement of processing capacity in the form of microprocessor(s) and memory in the form of memory circuits. Such arrangements are known as such from the technology of analyzers and relating equipment. To convert a known optical instrument into an equipment according to the invention it may be necessary, in addition to the hardware modifications, to store into the memory means a set of machine-readable instructions that instruct the microprocessor(s) to perform the operations described above. Composing and storing into memory of such instructions involves known technology which, when combined with the teachings of this patent application, is within the capabilities of a person skilled in the art.

Above, an embodiment of the solution according to the invention has been described. The principle according to the invention can naturally be modified within the frame of the scope defined by the claims, for example, by modification of the details of the implementation and ranges of use.

For example, the invention is described as applied to AlphaScreen™ measurements. However, even if the invention has special advantages when applied to such measurements, the invention can as well be applied in other types of measurements, in which the length of life time relating to emission is long, such as >0.5 s, compared to the time required for shifting the sample plate. On the other hand, although the invention is described above as applied to a versatile instrument for performing several types of measurements, the invention can also be applied in more simple instrumentation for e.g. only one type of measurement, such as AlphaScreen™ measurement.

The present invention offers a possibility to perform activation and detection of separate samples simultaneously and thus achieve increased effectiveness of the measurements. However, the present invention is applicable also in measurements with sequential activation and detection.

In the above embodiments laser source has been mentioned as an illumination source in the inventive arrangement. However, also other illumination sources are applicable, such as xenon or halogen pulse lamps together with an optical filter. The above embodiments have included a photo-multiplier tube as a detector. However, many other types of detectors are also applicable. The detector may be e.g. a Charge Coupled Device (CCD) detector or camera. It is possible to achieve a high efficiency/sensitivity with a cooled CCD.

Also, although the invention has been described with reference to the various microtitration plates it is equally applicable to any form of sample arrangements like vials, discs or tubes. The samples may be, except liquids, also in other form, such as gels and filters.

Although the invention is described with an arrangement where light source and detector are located on the top measurement head, there is no reason why their location on the bottom measurement head should not work. It is also possible to use illumination from above and detection from below the sample or vice versa.

The present invention has advantages in large number of applications, such as research and clinical applications.

What is claimed is:

1. An optical measurement instrument for measuring samples, the optical measurement instrument comprising:
   an illumination source for producing activation radiation,
   a detector for measuring emission radiation, and
   shifting means for changing relative position of the samples with respect to the illumination source and the detector,
wherein the shifting means are disposed to change the relative position of the samples with respect to the illumination source and the detector in a stepwise manner from a first relative position, in which the detector is capable of measuring the emission radiation from a first sample and the illumination source is capable of producing the activation radiation into a second sample, to a second relative position, in which the detector is capable of measuring the emission radiation from the second sample and the illumination source is capable of producing the activation radiation into a third sample.

2. An optical measurement instrument according to claim 1, wherein the illumination source and the detector are disposed to simultaneously measure the emission radiation from the first sample and produce the activation radiation into the second sample when the samples are in the first relative position with respect to the illumination source and the detector.

3. An optical measurement instrument according to claim 1, wherein the illumination source and the detector are disposed to sequentially measure the emission radiation from the first sample and produce the activation radiation into the second sample when the samples are in the first relative position with respect to the illumination source and the detector.

4. An optical measurement instrument according to claim 1, wherein the detector is disposed to measure chemiluminescence radiation.

5. An optical measurement instrument according to claim 1, wherein the illumination source and the detector are disposed to apply an Amplified Luminescent Proximity Homogeneous Assay—analysing method.

6. An optical measurement instrument according to claim 1, wherein the detector is one of the following: a photo-multiplier tube and Charge Coupled Device.

7. An optical measurement instrument according to claim 1, wherein the illumination source is laser light source.

8. An optical measurement instrument according to claim 1, wherein the shifting means are disposed to change the relative position of the samples with respect to the illumination source and the detector at each step by a distance that equals to a distance between two adjacent samples.

9. An optical measurement instrument according to claim 1, wherein the shifting means are disposed to change the relative position of the samples with respect to the illumination source and the detector at each step by a distance that equals to a multiple of a distance between two adjacent samples.

10. An optical measurement instrument according to claim 1, comprising another illumination source for producing another activation radiation and another detector for measuring another emission radiation, the other detector being disposed to measure the other emission radiation from a fourth sample as a response to a situation in which the other illumination source is producing the other activation radiation into the fourth sample.

11. An optical measurement instrument according to claim 10, wherein the other detector is disposed to measure photoluminescence radiation.

12. An optical measurement instrument according to claim 10, wherein the other detector is one of the following: a photo-multiplier tube and Charge Coupled Device.

13. An optical measurement instrument according to claim 10, wherein the other illumination source is laser light source.

14. A method for optical measurement of samples, the method comprising:
   producing activation radiation with an illumination source,
   measuring emission radiation with a detector, and
   changing relative position of the samples with respect to the illumination source and the detector in a stepwise manner from a first relative position, in which the detector is capable of measuring the emission radiation from a first sample and the illumination source is capable of producing the activation radiation into a second sample, to a second relative position, in which the detector is capable of measuring the emission radiation from the second sample and the illumination source is capable of producing the activation radiation into a third sample.

15. A method according to claim 14, wherein the emission radiation from the first sample is measured simultaneously with producing the activation radiation into the second sample when the samples are in the first relative position with respect to the illumination source and the detector.

16. A method according to claim 14, wherein the emission radiation from the first sample is measured sequentially with producing the activation radiation into the second sample when the samples are in the first relative position with respect to the illumination source and the detector.

17. A method according to claim 14, wherein the emission radiation is chemiluminescence radiation.

18. A method according to claim 14, wherein an Amplified Luminescent Proximity Homogeneous Assay—analysing method is applied with the illumination source and the detector.

19. A method according to claim 14, wherein the detector is one of the following: a photo-multiplier tube and Charge Coupled Device.

20. A method according to claim 14, wherein the illumination source is laser light source.

21. A method according to claim 14, wherein the relative position of the samples with respect to the illumination source and the detector is changed at each step by a distance that equals to a distance between two adjacent samples.

22. A method according to claim 14, wherein the relative position of the samples with respect to the illumination source and the detector is changed at each step by a distance that equals to a multiple of a distance between two adjacent samples.

23. A method according to claim 14, comprising producing another activation radiation with another illumination source into a fourth sample and measuring another emission radiation from the fourth sample with another detector simultaneously with producing the other activation radiation into the fourth sample.

24. A method according to claim 23, wherein the other emission radiation measured from the fourth sample is photoluminescence radiation.

25. A method according to claim 23, wherein the other detector is one of the following: a photo-multiplier tube and Charge Coupled Device.

26. A method to claim 23, wherein the other illumination source is laser light source.

\* \* \* \* \*